United States Patent [19]

Bloom et al.

[11] Patent Number: 4,784,576
[45] Date of Patent: Nov. 15, 1988

[54] PUMP PRESSURE SENSOR

[75] Inventors: Richard M. Bloom, Seminole, Fla.; Carl Ritson, San Jose, Calif.; Hal C. Danby, Sudbury, England

[73] Assignee: Critikon, Inc., San Jose, Calif.

[21] Appl. No.: 25,681

[22] Filed: Mar. 13, 1987

Related U.S. Application Data

[63] Continuation-in-part of Ser. No. 902,616, Sep. 2, 1986.

[51] Int. Cl.⁴ .................... F01B 25/26; F01B 31/12; F04B 21/00
[52] U.S. Cl. ............................ 417/63; 91/1; 92/5 R; 604/64; 604/131; 604/152; 604/153; 128/DIG. 13; 73/753
[58] Field of Search ............... 417/1, 18, 44, 63, 415, 417/478, 38, 219, 413; 91/1; 92/5 R; 361/283; 604/65, 118, 121, 131, 151, 152, 153; 128/DIG. 1, DIG. 12, DIG. 13, 672, 675, 722; 73/714, 753, 718

[56] References Cited

U.S. PATENT DOCUMENTS 4,056,333 11/1977 Lundquist .................... 417/63 X
4,565,497 1/1986 Miller et al. ..................... 417/63

FOREIGN PATENT DOCUMENTS

437199 8/1948 Italy .................................. 417/63
934259 6/1982 U.S.S.R. ............................. 73/753

Primary Examiner—Robert E. Garrett
Assistant Examiner—M. A. Williamson
Attorney, Agent, or Firm—William B. Walker; W. Brinton Yorks, Jr.

[57] ABSTRACT

A back pressure sensor for a positive displacement pump comprises at least one flexible beam having a pivot end and a drive connector end, and a pump actuator mounted between the pivot end and the drive connector end. The pump actuator connects with a positive displacement member of a pump. At least one sensor beam is connected to the flexible beam at a mounting position between the distal end and vibration damping end thereof. A first capacitor plate is mounted on the flexible beam at a position adjacent to the pivot end thereof, and a second capacitor plate is mounted adjacent the distal end of the sensor beam in a position facing the first capacitor plate at a distance which permits a capacitance coupling between the capacitor plates. A vibration damping mass is secured to the vibration damping end of the sensor beam for damping drive motion vibrations in the sensor beam.

16 Claims, 5 Drawing Sheets

PUMP PRESSURE SENSOR

RELATIONSHIP TO COPENDING APPLICATION

This application is a continuation-in-part of copending application Ser. No. 902,616 filed Sept. 2, 1986 and concurrently filed application titled PUMP PRESSURE SENSOR by Carl Ritson and Hal C. Danby (25300), 3-13-87, the entire contents of both applications being hereby incorporated by reference in their entireties.

FIELD OF THE INVENTION

This invention relates to improvements in fluid delivery systems, and in particular to parenteral solution or intravenous pumps. Most particularly this invention relates to a pressure sensor which monitors the back pressure or pumping pressure of liquid pumping systems.

BACKGROUND OF THE INVENTION

Pumping systems for the delivery of fluids intravenously or intra arterially are well known in the prior art and are in widespread daily use in hospitals throughout the world. These systems are commonly used for the intravenous or intra arterial delivery of such fluids as glucose solutions and blood plasma, and for the delivery of drugs, all at controlled delivery rates based on the patient's need, and in the case of drugs, the drug concentration being delivered.

Pumping systems offer advantages of mobility and positive control of flow rates by pump motor control. The prior art pumps include both peristaltic pumps and other positive displacement pumps. Both have the disadvantage of possible patient injury if an obstruction prevents free flow of liquid to the patient. Pumping pressure then increases until the obstruction clears or the equipment fails. The high pressure present upon sudden clearance of the obstruction can cause serious injury to the patient.

DESCRIPTION OF THE PRIOR ART

U.S. Pat. No. 3,739,943 describes a parenteral solution pump with a pressure monitor.

Pumps which squeeze or apply a positive fluid displacement member against a tube or pumping chamber segments and which control fluid flow to and from the pumping chamber with further positively controlled tube pinching members including peristaltic pumps and similar systems are described in U.S. Pat. Nos. 4,199,307, 4,273,121, 4,290,346, and 4,515,589, for example. A combination of a peristaltic pump and a back pressure monitor is described in U.S. Pat. No. 4,460,355.

Syringe pumps are described in U.S. Pat. No. 3,739,943 using a disposable hypodermic syringe as the pumping chamber and with a back pressure monitor. A syringe pump is also disclosed in U.S. Pat. No. 4,515,591.

A piston pump with a radially segmented spring element is described in U.S. Pat. No. 4,276,004. Piston pumps with the piston or equivalent displacement member covered with an elastic rubber barrier to isolate the pump chamber from the drive members are described in U.S. Pat. Nos. 4,140,118, 4,336,800, 4,453,931, 4,453,932, 4,457,753, and 4,519,732. Most piston pumps have inlet and outlet check valves. One or both of the inlet and outlet check valves in U.S. Pat. Nos. 4,126,132 and 4,468,222 are open during a fluid priming step prior to loading the pumping cassette into the operating housing, and are automatically activated into an operational position by the insertion of the cassette into the housing. In U.S. Pat. No. 4,468,222, the disposable cassette comprises an elastic diaphragm defining one wall of the pumping chamber and inlet and outlet valve members having a one piece molded construction.

Diaphragm pumps usually have resilient diaphragm members which are connected to a drive member, and are usually combined with inlet and outlet check valves as described in U.S. Pat. Nos. 2,812,716 and 2,954,738. Diaphragm pumps comprising concentric cylindrical segments isolated from the pumping chamber with a rubber diaphragm are described in U.S. Pat. Nos. 1,923,970 and 3,200,757.

SUMMARY OF THE INVENTION

The back pressure sensor of this invention comprises at least one flexible beam having a pivot end and a drive connector end. A pivot means is positioned at the pivot end thereof. The flexible beam has a first mounting position and a pump actuator mounting position between the pivot end and the drive connector end. A drive connector means is provided on said drive connector end thereof for engaging a pump drive. A pump actuator means is connected to said pump actuator mounting position for connecting with a positive displacement member of a positive displacement pump. The sensor includes at least one sensor beam having a distal end and a vibration damping end, with a second mounting position between said distal end and vibration damping end. The second mounting position is secured to the first mounting position of the flexible beam by a non-rotational connection.

A first capacitor plate is mounted on the flexible beam at a position adjacent to the pivot end thereof, and a second capacitor plate is mounted adjacent the distal end of the sensor beam in a position facing the first capacitor plate at a distance which permits a capacitance coupling between the capacitor plates. A vibration damping means is secured to the vibration damping end of the sensor beam for damping drive motion vibrations in the sensor beam.

The preferred vibration damping means is a mass which is secured to the sensor beam at a distance from the second mounting position which is sufficient to balance the mass of the second capacitor plate and the portion of the sensor beam extending from the first mounting position to the distal end thereof during the drive motion cycle. Preferably, the first mounting position is substantially aligned with the position of the pump actuator means, and the mass is integral with the sensor beam. The non-rotatable connection can be a body which is integral with the flexible beam and the sensor beam.

In one embodiment of the invention, the sensor can have a first sensor beam on one side of the flexible beam and a second sensor beam which is parallel to the first sensor beam and positioned on the side of the flexible beam opposite to the first sensor beam. The flexible beam can comprise first and second substantially parallel flexible beam portions extending from a crossbar to the pivot ends thereof, the ends of crossbar comprising the first mounting position. The pivot ends can be connected by a crossbar upon which the first capacitor plate is mounted. A single flexible beam portion can extend from the crossbar to the drive connector end thereof.

A pump-pressure sensor combination of this invention comprises a positive displacement pump and the pressure sensor described above, the pump comprising a pumping chamber for containing liquid to be pumped and a positive displacement member means for expelling liquid from the pumping chamber. The positive displacement member means connects with said pump actuator means. With this combination, increasing pressure in the pumping chamber effects an increasing flexure of the flexible beam and changes the distance between the capacitor plates.

DETAILED DESCRIPTION OF THE INVENTION

The back pressure sensor is a highly effective system for continuously monitoring the pressure in a pumping chamber during the positive displacement phase of the pumping cycle. It can be easily incorporated into any positive displacement pumping system where back pressure monitoring is important and particularly where excessive back pressure creates a serious hazard as with parenteral solution pumping systems. It is particularly advantageous for use in parenteral solution delivery pumping systems such as are described in copending application Ser. No. 902,616 filed Sept. 2, 1986.

Figure 1:
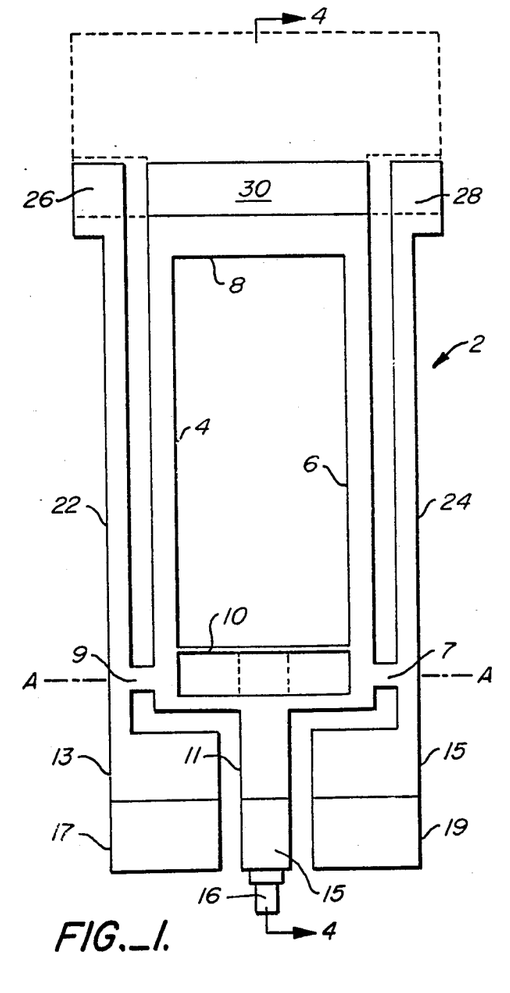
FIG. 1 is a front view of the sensor beam with the capacitor plates shown in dotted line representation.
Figure 2:
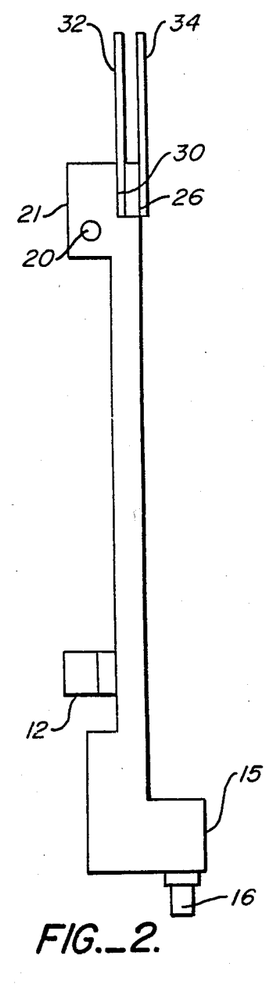
FIG. 2 is a side view of the sensor beam shown in FIG. 2 with the capacitor plates shown in solid line representation.
Figure 3:
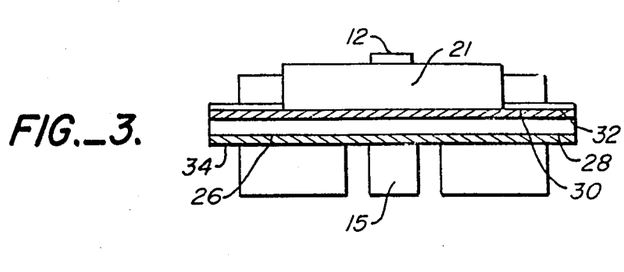
FIG. 3 is a top view of the sensor beam shown in FIG. 2 with the capacitor plates shown in solid line representation.

FIG. 1 shows a frontal view of one embodiment of the sensor assembly of this invention, and FIG. 2 and FIG. 3 are the side and top views thereof, respectively. The key to this assembly are one or more flexible beams which are flexed by back pressure and one or more sensor beams which remain unflexed. The distance between capacitor plates mounted on the flexible and sensor beams changes as the flexible beams are flexed. The change in capacitance produced by the change in capacitor plate spacing is functionally related to the amount of back pressure, and by monitoring the capacitance changes during the pumping cycle, data about the back pressure is obtained. The device can be used with conventional control systems which will give an alarm and/or shut down the pumping system. These can be activated when and if the capacitance (and back pressure) reaches a value predetermined to indicate a hazardous condition.

The sensor assembly 2 comprises, in the view shown in FIG. 1, a flexible left beam 4 and a flexible right beam 6 joined at their pivot ends by a pivot end crossbar 8. Beams 4 and 6 are joined at their proximal end by mounting crossbar 10 having a pumping actuator projection 12 (FIG. 2 and FIG. 3) mounted thereon. The lower part of the flexible beam is a single beam 11 extending from the center of the crossbar 10 in a position aligned with the axis of the beam pair 4 and 6 and terminating in a drive connector end with a frontal projection 15 upon which drive bearing mount 16 is positioned. Movement of the drive bearing mount 16 pivots the beam assembly around pivot 20 (FIG. 2) in the rear extension 21 of the crossbar 8. This pivotal motion is translated to a linear pump actuating motion by projection 12, by which it is transmitted to a positive displacement pumping member such as a piston, compression member or diaphragm of a pump.

Left sensor beam 22 and right sensor beam 24 are securely mounted at intermediate mounting positions 7 and 9 on the ends of the crossbar 10 and extend parallel to the flexible beams 4 and 6 along the sides thereof. The mounting is fixed and rotation of the sensor beams around the mounting positions with respect to the flexible beams is prevented. Preferably the flexible and sensor beams are made of metal or a durable organic polymer having a requisite rigidity and torsion modulus and are integrally joined by a short connecting portion at the mounting positions which is sufficiently thick to damp any torsion motion around the connecting portion.

The capacitor supporting ends of the sensor beams 22 and 24 have capacitor plate support surfaces 26 and 28 thereon. The front of the crossbar 8 also has a capacitor plate support surface 30 thereon. The relative position of the capacitor plates in the front view is shown by a dotted line representation, leaving the support surfaces unobscured for clarity.

The relative orientations of the mounted flexible beam capacitor plate 32 and sensor beam capacitor plate 34 are shown more clearly in FIG. 2 and FIG. 3 where the parallel capacitor plates are shown in solid line representations. The sensor beam capacitor plate 34 is shown mounted in front of the flexible beam capacitor plate 32, being supported by the supporting surfaces 26 and 28, and extends between the supporting surfaces 26 and 28 like a crossbar. The flexible beam capacitor plate 32 is shown positioned behind the capacitor plate 34, mounted on the single support surface 30 of the pivot crossbar 8. The distance between the parallel plates 32 and 34 is selected to provide an optimum capacitance coupling.

In an earlier sensor system described in copending application Serial No. 902,616 filed Sept. 2, 1986, vibratory movement of the sensor beams occurred which produced an oscillatory capacitance signal variation. The sensor beam construction of this invention is suitable for reducing or eliminating this signal variation. The sensor beams 22 and 24 are mounted to the flexible beam along the line A-A, in alignment with the crossbar 10 and actuator connector 12. The distal portions 13 and 15 of the sensor beams 22 and 24 have weighted masses 17 and 19 thereon. The weighted mass 17 is positioned to provide that the combined mass moments of the distal portion 13 and mass 17 counterbalance the combined mass moments of the portion of the flexible beam from the mounting position 9 to the distal end with supporting surface 26 and capacitor plate mass proportioned thereto during the pumping motion of the assembly. The weighted mass 19 is positioned to provide that the combined mass moments of the distal portion 15 and mass 19 counterbalance the combined mass moments of the portion of the flexible sensor beam 24 from the mounting position 7 to the distal end with supporting surface 28 and capacitor plate mass proportioned thereto during the pumping motion of the assembly.

Figure 4:
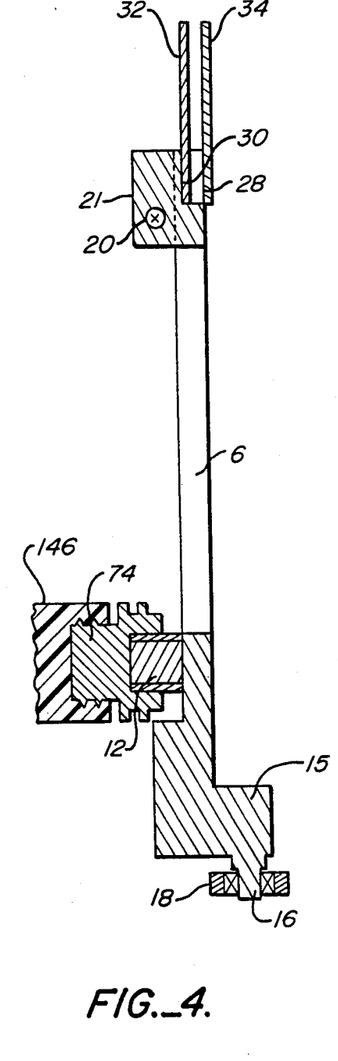
FIG. 4 is a cross-sectional view of the sensor beam, taken along the line 4—4 of FIG. 1 in the unflexed or relaxed position.
Figure 5:
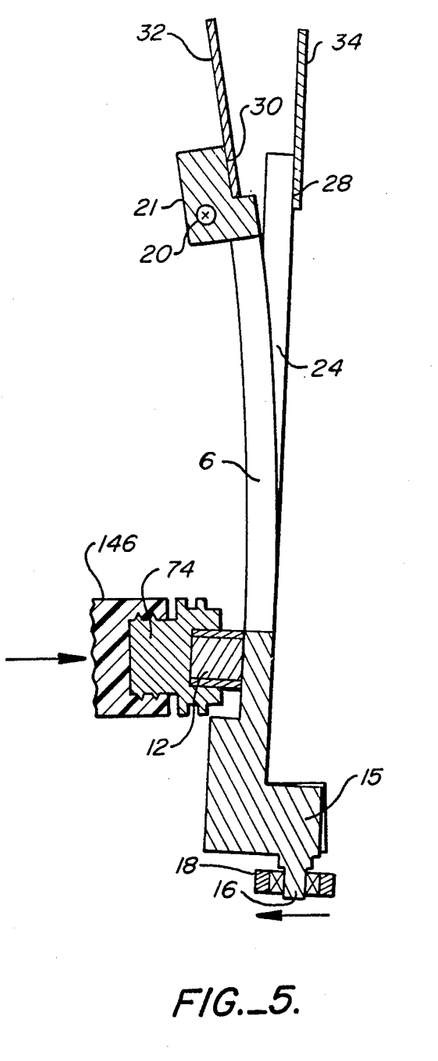
FIG. 5 is a cross-sectional view of the sensor beam of FIG. 4 as flexed under the influence of back pressure.
Figure 6:
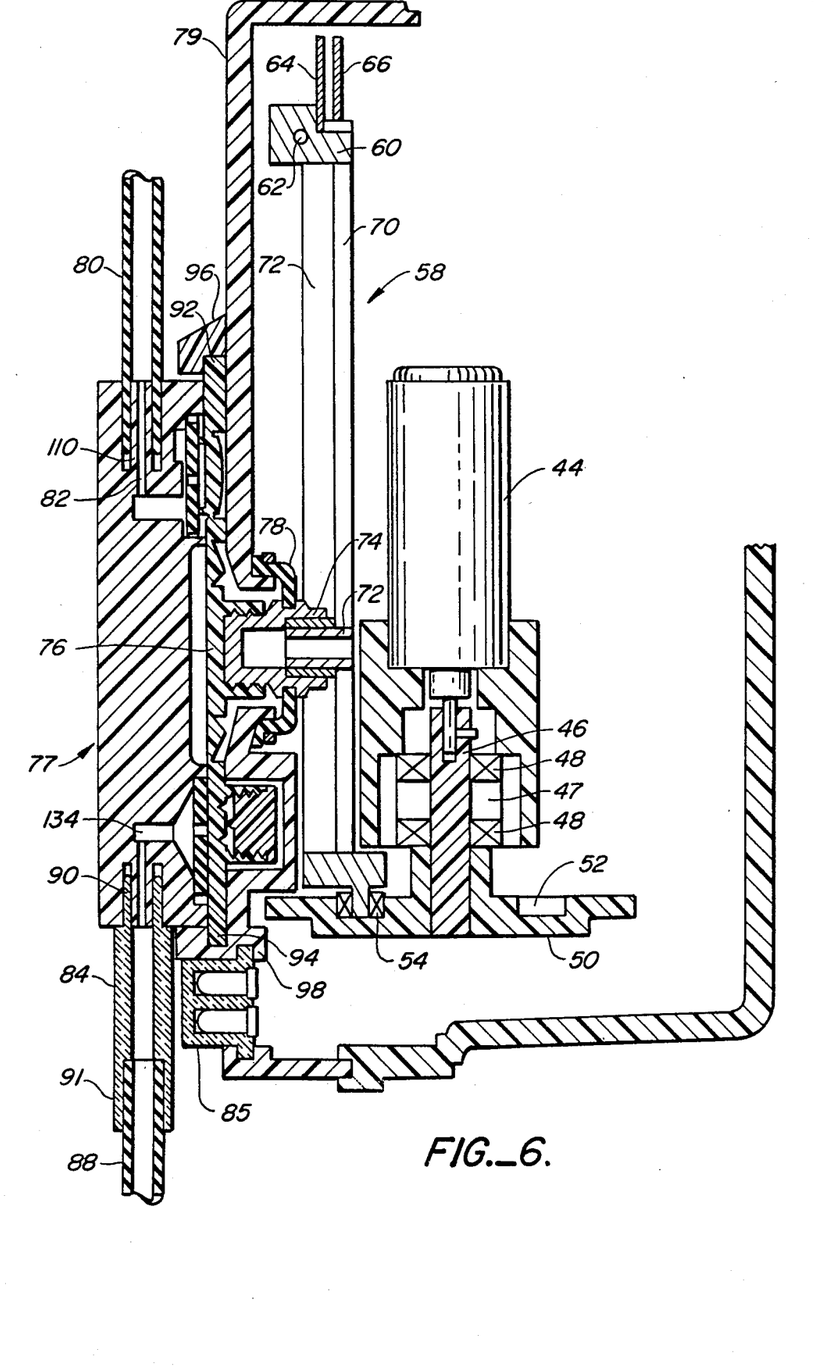
FIG. 6 is a partial cross-sectional representation of a pump combined with the back pressure sensor of this invention.

FIG. 4 is a cross-sectional view of the sensor beam assembly, taken along the line 4—4 of FIG. 1 in the unflexed or relaxed position, and FIG. 5 is a cross-sectional view of the sensor beam assembly with the flexible beam flexed under the influence of back pressure. The crossbar 8 and integral pivot ends of the flexible beams 4 and 6 are mounted for pivotal movement around the pivot 20. The lower end of the flexible beam 15 is driven through a reciprocating path by reciprocal movement of the drive bearing 18 and bearing support 16. As the bearing 18 is moved to the left, the pump actuator 12 with positive displacement member connecting elements 74 and 146 connected thereto moves to the left, transferring the movement to a pump displacement element (FIG. 5 and FIG. 6). Back pressure from the pumping chamber is realized by resistance to the movement of the actuator 12 to the left, that is, the pressure bears in the direction of the arrow against the actuator 12 and the corresponding crossbar 10. Beam flexure between the flexible beam ends shown in an exaggerated aspect in FIG. 5 thus occurs. The resulting curve of beams 4 and 6 displace the crossbar 30 and capacitor plate 32 mounted thereto to the left from the distal end of sensor beam 24 and capacitor plate 34, increasing the distance therebetween, and lowering the capacitance between the plates. The capacitor plates 32 and 34 can be connected to a pump control system such as is described in concurrently filed U.S. patent application No. (CRIK-103) filed concurrently herewith, the entire contents of which are hereby incorporated by reference. This pump control system provides a technique for measuring cassette compliance and depliance. The measured cassette compliance or depliance is used to determine the actual volume of fluid which was pumped during a pumping cycle, and this actual volume is then used to calibrate the pumping rate for precisely controlling the fluid delivery. Because the back pressure system is coupled directly to the drive assembly, the back pressure is reflected by capacitor plate distances throughout the pumping cycle. Therefore, an immediate signal is obtainable at any part of the cycle when the back pressure exceeds a level which has been predetermined to be hazardous. This alarm signal can also be used to shut off the system, sound an alarm or institute any other action desired.

FIG. 6 is a partial cross-sectional representation of one embodiment of a pump-pressure sensor combination of this invention. The DC motor 44 has a drive shaft 46 supported by bearing 48 with sprag clutch 47, the distal end of the drive shaft 46 being connected to a drive wheel 50. The drive wheel 50 has a cam groove 52 in the back face thereof engaged by the cam follower bearing 54 attached to the drive end of the sensor beam assembly 58. The opposite pivot end 60 of the drive beam 58 is mounted for pivotal movement around pin 62. The capacitor plates 64 and 66 are supported on the ends of the respective flexible beam 68 and sensor beam 70 as shown in detail in FIG. 1–5.

The drive actuator connector 72 is attached to a barbed, self-threading connector 74 (shown in detail in FIG. 7 and FIG. 8) and joined to a central portion of the flexible drive beam 70. The barbed, self-threading connector 74 engages a female receptor 76 integral with the central diaphragm plate on the back plate of the pump cassette 77. The flexible plate diaphragm is described in our copending application Ser. No. 799,235 filed Nov. 18, 1985, the entire contents of which are hereby incorporated by reference in its entirety.

The distance of the point of contact of the cam groove 52 and the cam follower 54 from the central axis of the drive shaft 46 varies as the drive shaft rotates, translating the rotary motion of the drive shaft to a reciprocating displacement of the cam follower drive bearing 54 and cassette drive connector 74. The drive connector 74 thus imparts a reciprocating motion to the diaphragm plate of which the female drive connector 76 is a part. A annular flexible splash shield 78 is secured to the male drive connector and the surrounding edges of the housing 79 to prevent liquid contaminants from reaching the interior of the housing 79.

Inlet tubing 80 from a liquid source (not shown) is secured to a tubing connector inlet 82 of the cassette 77. An optional air-in-line detector component 84 of this combination extends from connecting portion 90 in the bottom of the cassette 77 below the outlet valve cavity 134, communicating therewith. It faces a light source-detector array 85. The air-in-line detector is described in detail in our concurrently filed application titled AIR IN LINE DETECTOR by Hal C. Danby and Carl Ritson, (21191), 3-3-87, and the contents thereof are hereby incorporated in this application by reference in their entirety.

The cassette 77 is secured to the housing 79 by tabs or ears 92 and 94 extending from the cassette 77 into corresponding grooves defined by retention projections 96 and 98 extending from the front of the housing.

Details of the pump cassette elements an construction are described in concurrently filed application (25300), 3-13-87.

Figure 7:
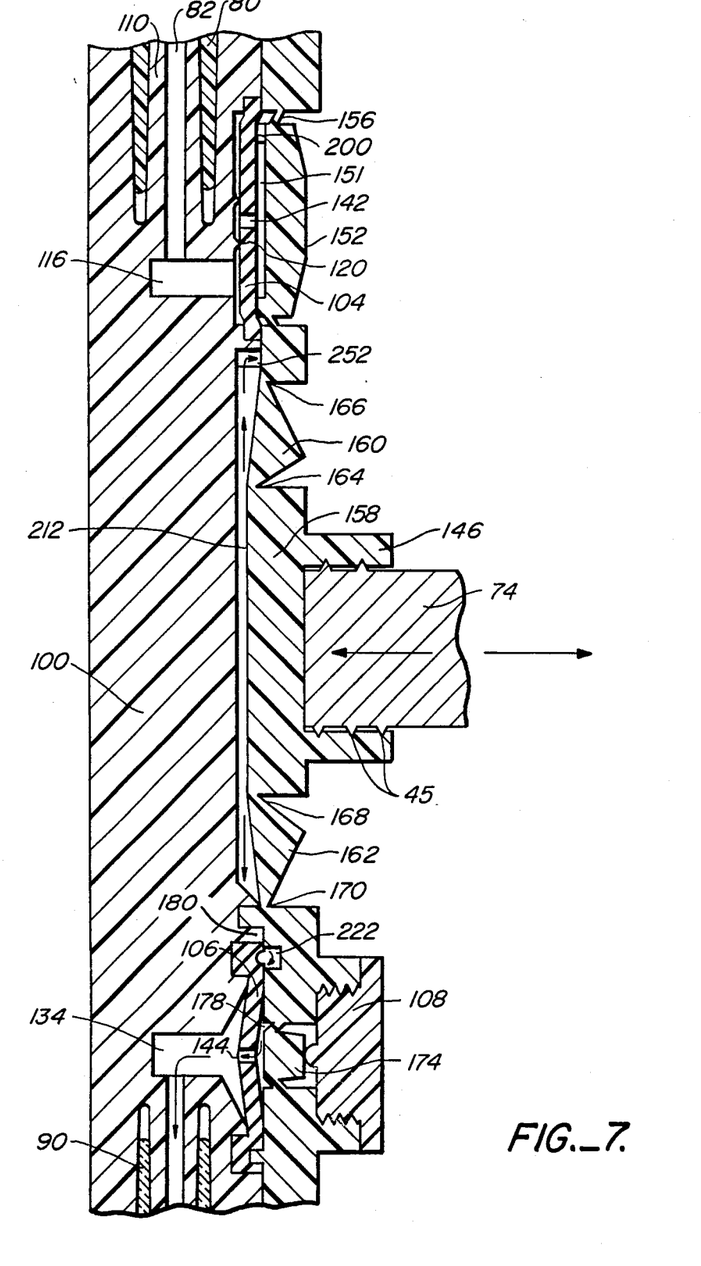
FIG. 7 is a partial cross-sectional view of the installed cassette assembly during the output phase of the pumping cycle.
Figure 8:
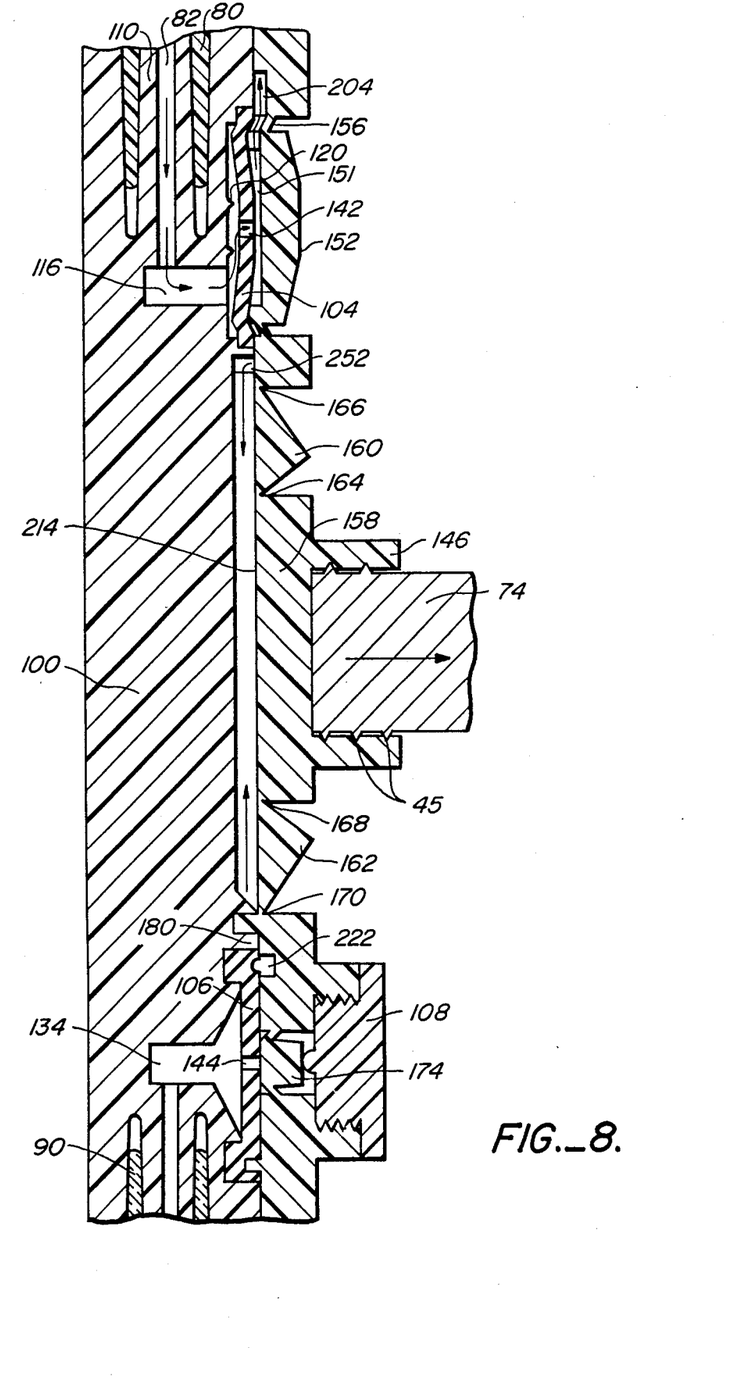
FIG. 8 is a partial cross-sectional view of the installed cassette assembly during the filling phase of the pumping cycle.

FIG. 7 is a partial cross-sectional view of the cassette assembly during the output phase of the pumping cycle, and FIG. 8 shows the cassette assembly during the filling phase of the pumping cycle. During the output phase, the motor drive element 74 advances toward the pumping cassette, moving the face 212 of the central diaphragm segment 158 toward the opposing face of the pump chamber cavity, thus reducing the volume of the pumping chamber. This movement is permitted by the flexure (with some stretching) of the hinge segments 164, 166, 168 and 170 and the corresponding movement of the rigid plate segments 160 and 162. The combination of the rigid plate segments and small area of the hinges prevents any significant distortion of the pumping chamber volume due to flexure of the pumping surfaces in the manner of resilient pump diaphragms. This pump thus combines the unique features of a diaphragm pump with the precision of a piston pump.

The fluid expressed from the pumping chamber is expelled through the outlet passageway 222 and 252 and eventually to the outlet check valve. The fluid pressure between the element 174 and the outlet check valve diaphragm 106 displaces the diaphragm surface from the surface of the element 174, exposing the diaphragm passageway 144. Liquid passes through opening 144 and cavity 134 to the air-in-line detector inlet 90. Reverse flow of liquid to the source is prevented by the construction of the inlet check valve. The volume 151 defined by the surface of the actuator 152, the ridge 200 and the inlet check valve diaphragm 104 is in direct communication with the pumping chamber, and the increased pressure of the output phase of the pump presses the diaphragm 104 securely against the seat 120, preventing fluid escape to the inlet passageway.

The back pressure in the system downstream of the pumping chamber, for example in the case of occlusion of a parenteral solution infusion needle, is transmitted by drive element 74. This increases the flexure of the flexible beam 6 (FIG. 4 and 5) and is reflected in the changes in capacitance between the capacitor plates 32 and 34.

The reverse flow of the filling phase of the pump is shown in FIG. 8. Reverse motion of the pump element 74 pulls the central rigid diaphragm segment 158 away from the opposing surface of the front plate, increasing the volume of the pumping chamber. The rigid, hinged plates 160 and 162 follow, the plate structure bending about the hinges 164, 166, 168 and 170. The rigid plate construction again achieves a volume change which is a direct function of the displacement of the actuator 74, achieving a precise filling volume.

The pressure in the pumping chamber and chamber 151 during the filling phase falls below the relative pressure in the inlet conduit 82 and inlet check valve inlet 116. The inlet fluid pressure displaces the face of the inlet check valve diaphragm 104 away from the valve seat 120, permitting liquid flow through the inlet check valve to the passageway 204 and to the pumping chamber. The pressure in the outlet chamber 134 exceeds the pressure in the pumping chamber during the filling phase, pressing the outlet check valve diaphragm 106 firmly against the surface of the outlet check valve element 174. Reverse flow of liquid from the outlet chamber 134 during the filling phase is thus prevented.

It will be readily apparent to a person skilled in the art that the back pressure sensor of this invention can be used with any positive displacement pump, and can be connected with the movable pumping actuator member in a variety of ways. A connection which is suitable for a piston pump or diaphragm pump may not be suitable for use with a syringe pump or peristaltic pump, for example. All suitable connections wherein the back pressure sensor system of this invention can be used are intended to be included within the invention.

Likewise, while the relative positions of the flexible and sensor beams and capacitor plates has been described with the flexible and sensor beams parallel whereby the increasing back pressure flexes the flexible beam away from the sensor beam, increasing the spacing between the capacitor plates, it will be readily apparent to a person skilled in the art that alternative and even opposite configurations can be devised within the scope of this invention. The flexible and sensor beams can be constructed at an angle to each other, and increasing pump pressure can cause the flexible beam to approach an orientation more parallel with the sensor beam. The distance between the capacitor plates thus can be designed to decrease with increasing pump back pressure. All such variations in the relationship between the flexible and sensor beams are intended to be included within the scope of this invention.

We claim:

1. A back pressure sensor comprising at least one flexible beam having a pivot end and a drive connector end, a pivot means positioned at the pivot end thereof, the flexible beam having a first mounting position and a pump actuator mounting position between the pivot end and the drive connector end, a drive connector means on said drive connector end thereof for engaging a pump drive, a pump actuator means connected to said pump actuator mounting position for connecting with a positive displacement member of a positive displacement pump, at least one sensor beam having a distal end and a vibration damping end, a second mounting position between said distal end and vibration damping end thereof secured to the first mounting position of the flexible beam by a non-rotational connection, a first capacitor plate mounted on the flexible beam at a position adjacent to the pivot end thereof, and a second capacitor plate mounted adjacent the distal end of the sensor beam in a position facing the first capacitor plate at a distance which permits a capacitance coupling between the capacitor plates, a vibration damping means secured to the vibration damping end of the sensor beam for damping drive motion vibrations in the sensor beam.

2. The back pressure sensor of claim 1 wherein the vibration damping means is a mass which is secured to the sensor beam at a distance from the second mounting position which is sufficient to balance the mass of the second capacitor plate and the portion of the sensor beam extending from the first mounting position to the distal end thereof during the drive motion cycle.

3. The back pressure sensor of claim 2 wherein the first mounting position is substantially aligned with the position of the pump actuator means.

4. The back pressure sensor of claim 2 wherein the mass is integral with the sensor beam.

5. The back pressure sensor of claim 1 wherein the non-rotatable connection is a body which is integral with the flexible beam and the sensor beam.

6. The back pressure sensor of claim 1 having a first sensor beam on one side of the flexible beam and a second sensor beam which is parallel to the first sensor beam and positioned on the side of the flexible beam opposite to the first sensor beam.

7. The back pressure sensor of claim 6 wherein the flexible beam comprises first and second substantially parallel flexible beam portions extending from a crossbar to the pivot ends thereof, the ends of crossbar comprising the first mounting position, the pivot ends being connected by a crossbar upon which the first capacitor plate is mounted.

8. The back pressure sensor of claim 6 wherein a single flexible beam portion extends from the crossbar to the drive connector end thereof.

9. A pump-pressure sensor combination of a positive displacement pump and the pressure sensor of claim 1 comprising a pumping chamber for containing liquid to be pumped, a positive displacement member means for expelling liquid from the pumping chamber, the positive displacement member means connecting with said pump actuator means, whereby increasing pressure in the pumping chamber effects an increasing flexure of the flexible beam and changes the distance between the capacitor plates.

10. A pump-pressure sensor combination of claim 9 wherein the vibration damping means is a mass which is secured to the sensor beam at a distance from the second mounting position which is sufficient to balance the mass of the second capacitor plate and the portion of the sensor beam extending from the first mounting position to the distal end thereof during the drive motion cycle.

11. A pump-pressure sensor combination of claim 10 wherein the first mounting position is substantially aligned with the position of the pump actuator means.

12. A pump-pressure sensor combination of claim 10 wherein the mass is integral with the sensor beam.

13. The pump-pressure sensor combination of claim 9 wherein the non-rotatable connection is a body which is integral with the flexible beam and the sensor beam.

14. The pump-pressure sensor combination of claim 9 having a first sensor beam on one side of the flexible beam and having a second sensor beam which is substantially parallel to the first sensor beam and positioned on the side of the flexible beam opposite to the first sensor beam.

15. The pump-pressure sensor combination of claim 14 wherein the flexible beam comprises first and second substantially parallel flexible beam portions extending from a crossbar to the pivot ends thereof, the ends of crossbar comprising the first mounting position, the pivot ends being connected by a crossbar upon which the first capacitor plate is mounted.

16. The pump-pressure sensor combination of claim 14 wherein a single flexible beam portion extends from the crossbar to the drive connector end thereof.

* * * * *